United States Patent
Yoshida et al.

(10) Patent No.: US 7,211,596 B2
(45) Date of Patent: May 1, 2007

(54) STABLE HIGH-CONCENTRATION INJECTION CONTAINING PYRAZOLONE DERIVATIVE

(75) Inventors: Hiroshi Yoshida, Tokyo (JP); Naoki Matsuo, Tokyo (JP); Masatoshi Chiba, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 469 days.

(21) Appl. No.: 10/477,275

(22) PCT Filed: May 9, 2002

(86) PCT No.: PCT/JP02/04508

§ 371 (c)(1),
(2), (4) Date: Dec. 11, 2003

(87) PCT Pub. No.: WO02/092082

PCT Pub. Date: Nov. 21, 2002

(65) Prior Publication Data

US 2004/0162330 A1  Aug. 19, 2004

(30) Foreign Application Priority Data

May 11, 2001  (JP) ............................. 2001-141683

(51) Int. Cl.
*A61K 31/4152* (2006.01)
(52) U.S. Cl. ..................................................... 514/404
(58) Field of Classification Search ................ 514/404
See application file for complete search history.

(56) References Cited

U.S. PATENT DOCUMENTS 4,857,542 A * 8/1989 Nishi et al. ................. 514/404
5,089,515 A * 2/1992 Morinaka et al. ........... 514/404
5,837,723 A * 11/1998 Watanabe .................... 514/404
6,933,310 B1 * 8/2005 Ikeda .......................... 514/403
2003/0109566 A1   6/2003 Mano et al.

FOREIGN PATENT DOCUMENTS

| EP | 0 208 874 A1 | 1/1987 |
| EP | 0 633 025 A1 | 1/1995 |
| JP | 52-031820 A | 3/1977 |
| JP | 63-132833 A | 6/1988 |
| WO | WO 96/29064 A1 | 9/1996 |
| WO | WO 02/00260 A1 | 1/2002 |

OTHER PUBLICATIONS

NIMOTOP® Drug Package Insert, "NIMOTOP® 30 mg Tablets; NIMOTOP® IV Solution," http://home.intekom.com/pharm/bayer/nimostop.html (Aug. 4, 2000).

Takeo, "The effect of MCI-186 on ischemic-reperfusion injury during cardiopulmonary bypass," *Okayama Igakkai Zasshi*, 105 (1/2), 217-226 (1993) (Abstract Only).

Singhai et al., "Cosolvent solubilization and formulation of an aqueous injection of ketoprofen," *Pharmazie*, 51 (10), 737-740 (1996).

\* cited by examiner

*Primary Examiner*—Kamal A. Saeed
(74) *Attorney, Agent, or Firm*—Leydig, Voit & Mayer, Ltd.

(57) ABSTRACT

An injection which contains as the active ingredient a pyrazolone derivative which typically is Edaravone, a physiologically acceptable salt thereof, or a hydrate or solvate of either in an amount of 3 to 60 mg/mL. It is excellent in long-term stability, product storage, and suitability for use.

25 Claims, No Drawings

STABLE HIGH-CONCENTRATION INJECTION CONTAINING PYRAZOLONE DERIVATIVE

TECHNICAL FIELD

This invention relates to an injection containing, as a main component, a high concentration of a pyrazolone derivative of the following formula (I):

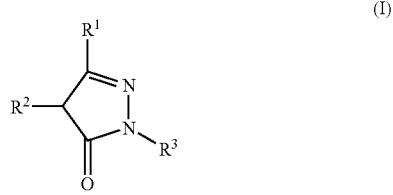

(wherein $R^1$ represents hydrogen atom, an aryl, an alkyl having 1 to 5 carbon atoms or an alkoxycarbonylalkyl having 3 to 6 carbon atoms in total, $R^2$ represents hydrogen atom, an aryloxy, an arylmercapto, an alkyl having 1 to 5 carbon atoms or a hydroxyalkyl having 1 to 3 carbon atoms, or $R^1$ and $R^2$ are coupled together to form an alkylene having 3 to 5 carbon atoms, and $R^3$ represents hydrogen atom, an alkyl having 1 to 5 carbon atoms, a cycloalkyl having 5 to 7 carbon atoms, a hydroxyalkyl having 1 to 3 carbon atoms, benzyl, a naphthyl or phenyl, or a phenyl substituted by 1 to 3 substituents which may be the same or different, and selected from the group consisting of an alkoxy having 1 to 5 carbon atoms, a hydroxyalkyl having 1 to 3 carbon atoms, an alkoxycarbonyl having 2 to 5 carbon atoms in total, an alkylmercapto having 1 to 3 carbon atoms, an alkylamino having 1 to 4 carbon atoms, a dialkylamino having 2 to 8 carbon atoms in total, a halogen atom, trifluoromethyl, carboxyl, cyano, hydroxyl group, nitro, amino and acetamido), or a physiologically acceptable salt thereof, or a hydrate or solvate thereof. In more detail, it relates to a long-stable and high-concentration injection comprising the aforementioned pyrazolone derivative or a physiologically acceptable salt thereof, or a hydrate or solvate thereof as an active ingredient.

BACKGROUND ART

3-Methyl-l-phenyl-2-pyrazolin-5-one (non-proprietary name: "Edaravone", trade name: "Radicut"; manufactured and sold by Mitsubishi Pharma Corporation. hereinafter referred to as Edaravone) which is one of the pyrazolone derivatives as mentioned above is also called 3-methyl-1-phenyl-5-pyrazolone. It is a compound recognized to have potent effectiveness in the various experiments using animal models of cerebrovascular disorders and its clinical application is extremely expected as a drug for the treatment of cerebrovascular disorders such as cerebral stroke, brain tumor, cerebral ischemia observed in the acute stage of head trauma, cerebral edema and the like for which no effective drug is available {brain function normalizing effect (Japanese patent publication (Kokoku) No. Hei 5-31523), lipid peroxidation inhibiting effect (Japanese patent publication (Kokoku) No. Hei 5-35128). An injection containing Edaravone as an active ingredient has been developed. One example is an injection which is an aqueous solution of Edaravone containing at least one compound selected from sulfites, hydrogensulfites and pyrosulfites, and a cysteine and has a pH in the range of 2.5 to 6.0 (Japanese patent publication (Kokoku) No. Hei 7-121861).

Now, Edaravone is clinically used as a brain protector (infusion) and two ampoules are needed daily. If Edaravone is prescribed for the other diseases in future, there are possibilities of using more ampoules. Anyway, in the present prescription, it is necessary to prepare at least two ampoules or vials a day. However, in the medical treatment site where any medical accidents must be avoided, the number of steps required for the preparation of medicines should be reduced as much as possible and the availability of the medicines should be increased. Further, medicines each composed of plural ampoules or vials need a wider space to store them in. Such a situation is not preferable for both a medicine maker and one engaged in the medical treatment.

There is accordingly a demand for the development of a medicine containing high-concentration of Edaravone but low in volume, namely, a high concentration low volume injection. However, Edaravone is sparingly soluble in water (2 mg/mL at 25° C.), has less chemical stability with an increase in its concentration in the aqueous solution, and is apt to be decomposed by oxidation in the aqueous solution compared to Edaravone in the powder form. In consideration of such properties, it is difficult to stabilize Edaravone as a pharmaceutical for a long period time and prepare an injection containing it in an amount exceeding a saturated solubility in water. Actually, such a formulation is not realized until now.

DISCLOSURE OF THE INVENTION

The present inventors made an intensive investigation on a high-concentration low volume injection containing as an active ingredient a pyrazolone derivative or physiologically acceptable salt thereof, or a hydrate or solvate thereof. As a result, it was found that ethanol had a superior solubilizing effect among various pharmaceutically acceptable additives usable for an injection and a solubility of the pyrazolone derivative or physiologically acceptable salt thereof, or hydrate or solvate thereof in ethanol drastically surpassed that in water. It was also found that ethanol was a superior solubilizer having high safety as an additive for injection and low reactivity with the pyrazolone derivative or physiologically acceptable salt thereof, or hydrate or solvate thereof (Test 1). When the chemical stability of a high concentration solution of the pyrazolone derivative or physiologically acceptable salt thereof, or hydrate or solvate thereof was investigated, however, coloration of the solution was observed, suggesting occurrence of some kind of reaction in the solution. The present inventors have proceeded with an investigation. As a result, it has been found that the stability of the pyrazolone derivative or physiologically acceptable salt thereof, or hydrate or solvate thereof is extremely improved by the addition of a stabilizing agent (Test 2), leading to completion of the present invention.

Namely, the gist of the present invention is as follows:
1. An injection comprising 3 to 60 mg/mL, per total volume of the injection, of a pyrazolone derivative of the following formula (I)

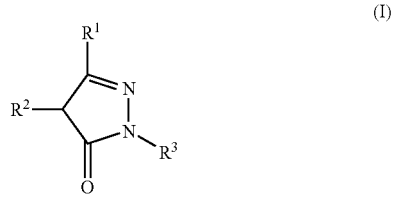

(wherein $R^1$ represents hydrogen atom, an aryl, an alkyl having 1 to 5 carbon atoms or an alkoxycarbonylalkyl having 3 to 6 carbon atoms in total; $R^2$ represents hydrogen atom, an aryloxy, an arylmercapto, an alkyl having 1 to 5 carbon atoms or a hydroxyalkyl having 1 to 3 carbon atoms, or $R^1$ and $R^2$ are coupled together to form an alkylene having 3 to 5 carbon atoms, and $R^3$ is hydrogen atom, an alkyl having 1 to 5 carbon atoms, a cycloalkyl having 5 to 7 carbon atoms, a hydroxyalkyl having 1 to 3 carbon atoms, benzyl, a naphthyl or phenyl, or a phenyl substituted by 1 to 3 substituents, which may be the same or different and selected from the group consisting of an alkoxy having 1 to 5 carbon atoms, a hydroxyalkyl having 1 to 3 carbon atoms, an alkoxycarbonyl having 2 to 5 carbon atoms in total, an alkylmercapto having 1 to 3 carbon atoms, an alkylamino having 1 to 4 carbon atoms, a dialkylamino having 2 to 8 carbon atoms in total, a halogen atom, trifluoromethyl, carboxyl, cyano, hydroxyl group, nitro, amino and acetamido) or physiologically acceptable salt thereof, or a hydrate or solvate thereof.
2. The injection wherein the pyrazolone derivative is 3-methyl-1-phenyl-2-pyrazolin-5-one.
3. The injection, further comprising ethanol.
4. The injection comprising 10 to 70 v/v % of ethanol based on the total amount of the injection.
5. The injection having a pH of from 2.0 to 6.5.
6. The injection having a pH of from 3.0 to 4.5.
7. The injection further comprising a pharmaceutically acceptable stabilizer.
8. The injection, wherein the pharmaceutically acceptable stabilizer is added in an amount of from 0.01 to 1 mg/ml based on the total amount of the injection.
9. The injection, wherein the pharmaceutically acceptable stabilizer is a chelating agent.
10. The injection, wherein the chelating agent is at least one selected from ethylenediamine, calcium disodium edetate and disodium edetate.

The process for preparing the injection mentioned above will be explained below. First, a pyrazolone derivative or physiologically acceptable salt thereof, or a hydrate or solvate thereof is dissolved in ethanol. Another solution is prepared by adding a stabilizer to a buffer adjusted to pH 2.0 to 6.5 to dissolve the former in the latter. Both solutions are mixed with stirring. If pH undergoes an extensive change after stirring, it is adjusted to 2.0 to 6.5 with a suitable acid or an alkali again. Then, the solution is sterilized, and hermetically filled in a suitable vessel (ampoule, vial etc.), whereby the injection of the present invention can be obtained.

The concentration of the pyrazolone derivative or physiologically acceptable salt thereof, or hydrate or solvate thereof used in the present invention is adjustable in the range of from 3 mg to 60 mg/mL by the amount of ethanol added as a solubilizer. Accordingly, the concentration of ethanol to be added as the solubilizer may be adjusted by the concentration of the pyrazolone or physiologically acceptable salt, or hydrate or solvate thereof to be dissolved. If the concentration of ethanol is too low, its solubilizing effect on the pyrazolone derivative or physiologically acceptable salt thereof, or hydrate or solvate thereof is reduced. On the contrary, a too high concentration poses a problem upon preparation of the injection such as difficulty in the adjustment of the liquid amount, because it increases a volatility. Consequently, the concentration of ethanol is 10 to 70 v/v % per total volume of the injection, preferably 15 to 55 v/v %, more preferably 20 to 40 v/v %. Any pharmaceutically acceptable agent is usable as the stabilizer to be added, but a chelating agent is preferred. Any pharmaceutically acceptable chelating agents are usable as the chelating agent of the present invention, but ethylenediamine, calcium disodium edetate or disodium edetate is preferred. Of these, disodium edetate is more preferred. The concentration of the stabilizer is preferably 0.01 to 1 mg/mL, especially 0.05 to 0.5 mg/mL. If the amount of the stabilizer is below the above-described range, its stabilizing effect on the pyrazolone derivative or physiologically acceptable salt thereof, or hydrate or solvate thereof is not sufficient. If the amount of the stabilizer exceeds the range, the stabilizing effect has reached its ceiling and further such amount is not preferable in view of safety. The pH of the injection of the present invention is preferably adjusted to 2.0 to 6.5, especially 3.0 to 4.5 with a pharmaceutically acceptable buffer for an injection such as citric acid or a salt thereof, phosphoric acid or a salt thereof, acetic acid or a salt thereof or the like in view of the stability of the pyrazolone derivative or physiologically acceptable salt thereof, or hydrate or solvate thereof. The injection of the present invention can also be prepared by adding a pharmaceutically acceptable isotonizing agent, a preservative and the like as needed.

BEST MODES FOR CARRYING OUT THE INVENTION

The present invention will be explained in more detail. It should however be borne in mind that the present invention is not limited by the following examples without departing from the scope of the present invention.

EXAMPLE 1

Edaravone (1 g) was added to 60 mL of ethanol to dissolve the former in the latter. Separately, to 140 mL of water for injection were added 20 mg of disodium edetate, 420 mg of citric acid monohydrate and 294 mg of trisodium citrate to dissolve the latter in the former. These two solutions were mixed with stirring and the mixed solution was adjusted to pH 3.6 with 1 mol/L of hydrochloric acid. Then, water for injection was added to give a total volume of 200 mL, followed by aseptic filtration through a membrane filter. The solution thus obtained was filled into a 10 mL vial. After the air in the head space of the vial was purged with nitrogen, the vial was sealed hermetically with a rubber stopper and an aluminum cap to obtain an injection (the concentration of Edaravone: 5 mg/ml).

EXAMPLE 2

An injection was obtained by a similar procedure to Example 1 except that 196 mg of phosphoric acid was used in place of citric acid monohydrate and trisodium citrate.

COMPARATIVE EXAMPLE 1

Edaravone (1 g) was added to 100 mL of ethanol to dissolve the former in the latter. Then, water for injection was added to give a total volume of 200 mL, followed by aseptic filtration through a membrane filter. The solution thus obtained was filled into a 10 mL vial. After the air in the head space was purged with nitrogen, the vial was sealed hermetically with a rubber stopper and an aluminum cap to obtain an injection.

COMPARATIVE EXAMPLE 2

Edaravone (1 g) was added to 200 mL of ethanol to dissolve the former in the latter. The resulting solution was subjected to aseptic filtration through a membrane filter. The solution thus obtained was filled into a 10 mL vial. After the air in the head space was purged with nitrogen, the vial was sealed hermetically with a rubber stopper and an aluminum cap to obtain an injection.

COMPARATIVE EXAMPLE 3

An injection was obtained by a similar procedure to Comparative Example 1 except that propylene glycol was used in place of ethanol.

COMPARATIVE EXAMPLE 4

An injection was obtained by a similar procedure to Comparative Example 1 except that N,N-dimethylacetamide was used in place of ethanol.

COMPARATIVE EXAMPLE 5

An injection was obtained by a similar procedure to Example 1 without using disodium edetate.

COMPARATIVE EXAMPLE 6

An injection was obtained by a similar procedure to Example 1 except that 50 mg of thioglycerol was used in place of disodium edetate.

COMPARATIVE EXAMPLE 7

An injection was obtained by a similar procedure to Example 1 except that 70 mg of L-cysteine hydrochloride monohydrate and 140 mg of sodium hydrogen sulfite were used in place of disodium edetate, and 196 mg of phosphoric acid was used in place of citric acid monohydrate and trisodium citrate.

<Test 1>

"Confirmation of Solubility of Edaravone in Various Solubilizers and Their Reactivity with Edaravone"

Water for injection (5 mL) was added to 5 mL of each of ethanol, propylene glycol, polyethylene glycol 400 and N,N-dimethylacetamide widely used as a solubilizer for an intravenous injection, followed by stirring. Edaravone was added to the resulting aqueous solubilizer solution and the mixture was stirred in a thermostat maintained at 4° C. by using a stirrer at a fixed but not bubbling speed all day and night. After completion of the stirring, a portion of Edaravone which had remained undissolved was checked visually to confirm that each solution thus obtained was a saturated aqueous solution of Edaravone. Then, the solution was quickly filtered through a membrane filter (pore size: 0.45 μm) kept at 4° C. and the amount of Edaravone contained in the filtrate was measured by HPLC method as explained below. Further, the maximum amount of each of the solubilizers used a day as an injection for intravenous administration was also shown (Iyakuhin-tenkabutu-jiten 2000 (published by Yakuji-nippou-sha), p. 127, 264 and 229 to 230. The maximum amount of ethanol was calculated based on the amount used for NIMOTOP IV (registered trademark, Bayer Co.)) and its solubilizing effect on Edaravone was calculated as a numerical term. The results are shown in Table 1.

Measuring Method by HPLC and its Conditions:

By liquid chromatography (LC) using ethyl paraaminobenzoate as an internal standard substance, a peak area ratio of Edaravone to the internal standard substance was found and based on it, the concentration of Edaravone was determined.

Detector: Ultraviolet spectrophotometer (wavelength measured: 240 nm)

Column: A stainless tube having inside diameter of about 4 mm and length of about 15 cm and filled with octadecylsilylated silica-gel 5 μm was used at a fixed temperature near 50° C.

Mobile phase: A (3:1) mixed solution of 10 mM aqueous acetic acid solution and methanol, adjusted to pH 5.5 with aqueous ammonia Flow rate: adjusted so that the retention time of Edaravone would be about 8 minutes.

TABLE 1

| Solubilizer | Solubility of Edaravone (4° C.) | Maximum amount of solubilizer used | Evaluation of solubilizing effect Solubility (mg/mL) × maximum amount used (mL) |
|---|---|---|---|
| 50 v/v % Ethanol | 10 mg/mL | 50 mL | 500 |
| 50 v/v % Propylene glycol | 6 mg/mL | 3.2 mL | 19.2 |
| 50 v/v % Polyethylene glycol 400 | 13 mg/mL | 2.8 mL | 36.4 |
| 50 v/v % N,N-Dimethylacetamide | 20 mg/mL | 0.32 mL | 6.4 |

Further, the injections obtained by Comparative Examples 1 to 4 were kept in a thermostat at 60° C. and the degree of coloration of the solutions was checked with the passage of time (Table 2).

TABLE 2

| Sample | Solubilizer | Coloration of the solution |
|---|---|---|
| Comparative Example 1 | Ethanol | Colorless and transparent without any change after 10 days |
| Comparative Example 2 | Ethanol | Colorless and transparent without any change after 10 days |
| Comparative Example 3 | Propylene glycol | Change to yellow on Day 1 |
| Comparative Example 4 | N,N-Dimethylacetamide | Change to yellow on Day 1 |

From the results as above, it has been proved that ethanol is a superior solubilizer and at the same time, a superior additive because it does not cause coloration of the solution and it has low reactivity with Edaravone.

<Test 2>

"Confirmation of the Superiority of the Stabilizer for Edaravone"

The injections obtained by Examples 1 to 2 and Comparative Examples 5 to 7 were maintained in a thermostat at 40° C. or 60° C. and the amount of decomposed products with the passage of time was measured by the following HPLC method. The total amount of the decomposed products after storage for a predetermined period of time was shown in Table 3.

Measuring Method by HPLC and its Conditions:

The total amount of the decomposed products was indicated using a percentage of the total area of each analogous decomposed products to a peak area of Edaravone (measured in accordance with the two conditions), each determined by liquid chromatography (LC).

Detector: Ultraviolet spectrophotometer (wavelength measured: 240 nm)

Column: A stainless tube having inside diameter of about 4 mm and length of about 15 cm and filled with octadecylsilylated silica-gel 5 μm was used at a fixed temperature near 40° C.

Mobile phase: (1) A (100:100:1) mixed solution of water, methanol and glacial acetic acid (2) A (3:1) mixed solution of a 10 mM aqueous acetic acid solution and methanol, adjusted to pH 5.5 with aqueous ammonia Flow rate: (1) adjusted so that the retention time of Edaravone would be about 4 minutes.

(2) adjusted so that the retention time of Edaravone would be about 11 minutes.

TABLE 3

| Sample | After storage at 40° C. for 2 months | After storage at 60° C. for 1 month |
| --- | --- | --- |
| Example 1 | 0.34% | 1.22% |
| Example 2 | 0.35% | 1.14% |
| Comparative Example 5 | 1.25% | — |
| Comparative Example 6 | 1.03% | — |
| Comparative Example 7 | 0.48% | 2.60% |

It has been proved that the injection excellent in long-term stability can be prepared by adding the stabilizer.

INDUSTRIAL APPLICABILITY

From the above, the injection of the present invention is a high concentration low volume solution-type injection containing the pyrazolone derivative or physiologically acceptable salt thereof, or hydrate or solvate thereof as an active ingredient. It is excellent in long-term stability, product storage, and suitability for use.

The present application was filed with claiming the conventional priority based on Japanese Patent Application No. 2001-41683.

The invention claimed is:

1. An injectable pharmaceutical composition comprising water and 3 to 60 mg/mL, per total volume of the injectable pharmaceutical composition, of a pyrazolone derivative of the following formula (I):

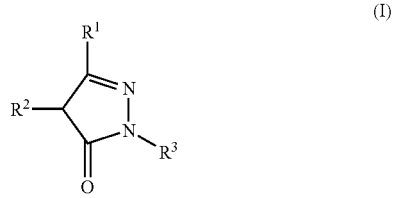

(I)

wherein $R^1$ represents hydrogen atom, an aryl, an alkyl having 1 to 5 carbon atoms or an alkoxycarbonylalkyl having 3 to 6 carbon atoms in total, $R^2$ represents hydrogen atom, an aryloxy, an arylmercapto, an alkyl having 1 to 5 carbon atoms or a hydroxyalkyl having 1 to 3 carbon atoms, or $R^1$ and $R^2$ is coupled together to form an alkylene having 3 to 5 carbon atoms, and $R^3$ represents hydrogen atom, an alkyl having 1 to 5 carbon atoms, a cycloalkyl having 5 to 7 carbon atoms, a hydroxyalkyl having 1 to 3 carbon atoms, benzyl, naphthyl, phenyl, or a phenyl substituted with 1 to 3 substituents, which may be the same or different and are selected from the group consisting of an alkoxy having 1 to 5 carbon atoms, a hydroxyalkyl having 1 to 3 carbon atoms, an alkoxycarbonyl having 2 to 5 carbon atoms in total, an alkylmercapto having 1 to 3 carbon atoms, an alkylamino having 1 to 4 carbon atoms, a dialkylamino having 2 to 8 carbon atoms in total, a halogen atom, trifluoromethyl, carboxyl, cyano, hydroxyl group, nitro, amino, and) acctamido, or physiologically acceptable salt thereof, or a hydrate or solvate thereof.

2. The injectable pharmaceutical composition of claim 1, wherein the pyrazolone derivative is 3-methyl-1-phenyl-2-pyrazolin-5-one.

3. The injectable pharmaceutical composition of claim 1, wherein the injectable pharmaceutical composition further comprises ethanol.

4. The injectable pharmaceutical composition of claim 3, wherein ethanol is present in an amount of from 10 to 70 v/v % ethanol per total volume of the injectable pharmaceutical composition.

5. The injectable pharmaceutical composition of claim 1, wherein the injectable pharmaceutical composition has a pH of from 2.0 to 6.5.

6. The injectable pharmaceutical composition of claim 5, wherein the injectable pharmaceutical composition has a pH of from 3.0 to 4.5.

7. The injectable pharmaceutical composition of claim 1, wherein the injectable pharmaceutical composition further comprises a pharmaceutically acceptable stabilizer.

8. The injectable pharmaceutical composition of claim 7, wherein the pharmaceutically acceptable stabilizer is present in an amount of from 0.01 to 1 mg/ml per total volume of the injectable pharmaceutical composition.

9. The injectable pharmaceutical composition of claim 7, wherein the pharmaceutically acceptable stabilizer is a chelating agent.

10. The injectable pharmaceutical composition of claim 9, wherein the chelating agent is at least one chelating agent selected from the group consisting of ethylenediamine, calcium disodium edetate, and disodium edetate.

11. The injectable pharmaceutical composition of claim 1, wherein the injectable pharmaceutical composition further comprises ethanol and has a p11 of from 2.0 to 6.5.

12. The injectable pharmaceutical composition of claim 11, wherein the injectable pharmaceutical composition further comprises a pharmaceutically acceptable stabilizer that is at least one chelating agent selected from the group consisting of ethylenediamine, calcium disodium edetate, and disodium edetate.

13. The injectable pharmaceutical composition of claim 12, wherein the ethanol is present in an amount from 10 to 70 v/v % ethanol per total volume of the injectable pharmaceutical composition, and the pharmaceutically acceptable stabilizer is present in an amount of from 0.01 to 1 mg/ml per total volume of the injectable pharmaceutical composition.

14. The injectable pharmaceutical composition of claim 2, wherein the injectable pharmaceutical composition further comprises ethanol.

15. The injectable pharmaceutical composition of claim 14, wherein ethanol is present in an amount of from 10 to 70 v/v % ethanol per total volume of the injectable pharmaceutical.

16. The injectable pharmaceutical composition of claim 2, wherein the injectable pharmaceutical composition has a pH of from 2.0 to 6.5.

17. The injectable pharmaceutical composition of claim 16, wherein the injectable pharmaceutical composition has a pH of from 3.0 to 4.5.

18. The injectable pharmaceutical composition of claim 2, wherein the injectable pharmaceutical composition further comprises a pharmaceutically acceptable stabilizer.

19. The injectable pharmaceutical composition of claim 18, wherein the pharmaceutically acceptable stabilizer is present in an amount of from 0.01 to 1 mg/ml per total volume of the injectable pharmaceutical composition.

20. The injectable pharmaceutical composition of claim 18, wherein the pharmaceutically acceptable stabilizer is a chelating agent.

21. The injectable pharmaceutical composition of claim 20, wherein the chelating agent is at least one chelating agent selected from the group consisting of ethylenediamine, calcium disodium edetate, and disodium edetate.

22. The injectable pharmaceutical composition of claim 2, wherein the injectable pharmaceutical composition further comprises ethanol and has a pH of from 2.0 to 6.5.

23. The injectable pharmaceutical composition of claim 22, wherein the injectable pharmaceutical composition further comprises a pharmaceutically acceptable stabilizer that is at least one chelating agent selected from the group consisting of ethylenediamine, calcium disodium edetate, and disodium edetate.

24. The injectable pharmaceutical composition of claim 23, wherein the ethanol is present in an amount from 10 to 70 v/v % ethanol per total volume of the injectable pharmaceutical composition, and the pharmaceutically acceptable stabilizer is present in an amount of from 0.01 to 1 mg/ml per total volume of the injectable pharmaceutical composition.

25. The injectable pharmaceutical composition of claim 24, wherein the injectable pharmaceutical composition has a pH of from 3.0 to 4.5.

* * * * *